(12) United States Patent
Christensen et al.

(10) Patent No.: US 6,723,749 B2
(45) Date of Patent: Apr. 20, 2004

(54) FATTY ACID SYNTHASE INHIBITORS

(75) Inventors: Siegfried B. Christensen, King of Prussia, PA (US); Daniel J. Mercer, King of Prussia, PA (US); Jia-Ning Xiang, Wayne, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/343,558

(22) PCT Filed: Aug. 2, 2001

(86) PCT No.: PCT/US01/24460

§ 371 (c)(1), (2), (4) Date: Jan. 31, 2003

(87) PCT Pub. No.: WO02/09688

PCT Pub. Date: Feb. 7, 2002

(65) Prior Publication Data

US 2004/0058988 A1 Mar. 25, 2004

Related U.S. Application Data

(60) Provisional application No. 60/222,684, filed on Aug. 2, 2000.

(51) Int. Cl.$^7$ .................. A61K 31/19; A61K 31/135; A61K 31/18; A61K 31/13; C07C 63/00

(52) U.S. Cl. ............ 514/557; 514/570; 514/602; 514/603; 514/649; 514/651; 514/659; 562/405

(58) Field of Search .................. 514/557, 570, 514/602, 603, 649, 651, 659; 562/405

(56) References Cited

U.S. PATENT DOCUMENTS 5,952,381 A * 9/1999 Chen et al. ............. 514/565

* cited by examiner

*Primary Examiner*—Alan L. Rotman
*Assistant Examiner*—Taylor Victor Oh
(74) *Attorney, Agent, or Firm*—Soma G. Simon; Mary E. McCarthy; Charles M. Kinzig

(57) ABSTRACT

This invention relates to the use of compounds as inhibitors of the fatty acid synthase FabH.

4 Claims, No Drawings

FATTY ACID SYNTHASE INHIBITORS

This application claims the benefit of Provisional application Ser. No. 60/222,684, filed Aug. 2, 2000.

FIELD OF THE INVENTION

This invention relates to the use of compounds as inhibitors of the fatty acid synthase FabH.

BACKGROUND OF THE INVENTION

The pathway for the biosynthesis of saturated fatty acids is very similar in prokaryotes and eukaryotes. However, although the chemical reactions may not vary, the organization of the biosynthetic apparatus is very different. Vertebrates and yeasts possess type I fatty acid synthases (FASs) in which all of the enzymatic activities are encoded on one or two polypeptide chains, respectively. The acyl carrier protein (ACP) is an integral part of the complex. In contrast, in most bacterial and plant FASs (type II) each of the reactions are catalyzed by distinct monofunctional enzymes and the ACP is a discrete protein. Mycobacteria are unique in that they possess both type I and II FASs; the former is involved in basic fatty acid biosynthesis whereas the latter is involved in synthesis of complex cell envelope lipids such as mycolic acids. There therefore appears to be considerable potential for selective inhibition of the bacterial systems by broad-spectrum antibacterial agents (Jackowski, S. 1992. In Emerging Targets in Antibacterial and Antifungal Chemotherapy. Ed. J. Sutcliffe & N. Georgopapadakou. Chapman & Hall, New York; Jackowski, S. et al. (1989). J. Biol. Chem. 264, 7624–7629.)

The first step in the biosynthetic cycle is the condensation of malonyl-ACP with acetyl-CoA by FabH. In subsequent rounds malonyl-ACP is condensed with the growing-chain acyl-ACP (FabB and FabF, synthases I and II respectively). The second step in the elongation cycle is ketoester reduction by NADPH-dependent β-ketoacyl-ACP reductase (FabG). Subsequent dehydration by β-hydroxyacyl-ACP dehydrase (either FabA or FabZ) leads to trans-2-enoyl-ACP which is in turn converted to acyl-ACP by NADH-dependent enoyl-ACP reductase (FabI). Further rounds of this cycle, adding two carbon atoms per cycle, eventually lead to palmitoyl-ACP whereupon the cycle is stopped largely due to feedback inhibition of FabH and I by palmitoyl-ACP (Heath, et al, (1996), J.Biol.Chem. 271, 1833–1836). Fab H is therefore a major biosynthetic enzyme, which is also a key regulatory point in the overall synthetic pathway (Heath, R. J. and Rock, C. O. 1996. J.Biol.Chem. 271, 1833–1836; Heath, R. J. and Rock, C. O. 1996. J.Biol.Chem. 271, 10996–11000).

The antibiotic thiolactomycin has broad-spectrum antibacterial activity both in vivo and in vitro and has been shown to specifically inhibit all three condensing enzymes. It is non-toxic and does not inhibit mammalian FASs (Hayashi, T. et al.,1984. J. Antibiotics 37, 1456–1461; Miyakawa, S. et al., 1982. J. Antibiotics 35, 411–419; Nawata, Y et al., 1989. Acta Cryst. C45, 978–979; Noto, T. et al., 1982. J. Antibiotics 35, 401–410; Oishi, H. et al., 1982. J. Antibiotics 35, 391–396. Similarly, cerulenin is a potent inhibitor of FabB & F and is bactericidal but is toxic to eukaryotes because it competes for the fatty-acyl binding site common to both FAS types (D'Agnolo, G. et al.,1973. Biochim. Biophys. Acta. 326, 155–166). Extensive work with these inhibitors has proved that these enzymes are essential for viability. Little work has been carried out in Gram-positive bacteria There is an unmet need for developing new classes of antibiotic compounds that are not subject to existing resistance mechanisms. No marketed antibiotics are targeted against fatty acid biosynthesis, therefore it is unlikely that novel antibiotics of this type would be rendered inactive by known antibiotic resistance mechanisms. Moreover, this is a potentially broad-spectrum target. Therefore, FabH inhibitors would serve to meet this unmet need.

SUMMARY OF THE INVENTION

This invention comprises novel compounds and pharmaceutical compositions containing these compounds and their use as PabH inhibitors that are useful as antibiotics for the treatment of Gram positive and Gram negative bacterial infections.

This invention further constitutes a method for treatment of a Gram negative or Gram positive bacterial infection in an animal, including humans, which comprises administering to an animal in need thereof, an effective amount of a compound of this invention.

DETAILED DESCRIPTION OF THE INVENTION

The compounds of this invention are represented by Formula (I):

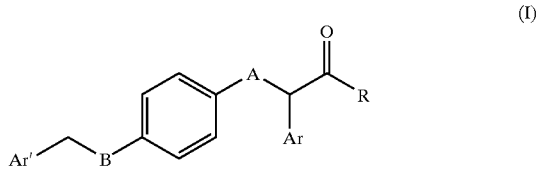

wherein:
R represents OH, or $NHSO_2R^2$;
A represents NH or O;
B represents O, or $NR^1$;
$R^1$ represents Ar'alkyl, or AlkylCO;
Ar and Ar' represent, independently, phenyl, thiophenyl, pyridinyl, or pyrimidinyl, all of which could be substituted with a substituting selected from the group consisting of: halo, including fluoro, bromo, chloro, iodo, $NO_2$, CN, $CO_2R^3$, $OR^3$, $NR^3R^4$, $C_{1-10}$alkyl, $C_{1-10}$alkoxy, aryloxy, arylalkoxy, and heteroaryloxy;
$R^2$ represents alkyl, Ar'alkyl, or Ar'; and
$R^3$ and $R^4$ represent, independently, hydrogen, or $C_{1-10}$alkyl.

Also included in the invention are pharmaceutically acceptable salt complexes.

As used herein, "alkyl" means both straight and branched chains of 1 to 6 carbon atoms, unless the chain length is otherwise limited, including, but not limited to, methyl, ethyl, n-propyl, iso-propyl, n-butyl, sec-butyl, iso-butyl, tert-butyl, n-pentyl and the like. The alkyl may carry substituents such as hydroxy, carboxy, alkoxy, and the like.

The compounds of this invention may contain one or more asymmetric carbon atoms and may exist in racemic and optically active forms. All of these compounds and diastereomers are contemplated to be within the scope of the present invention.

Some of the compounds of this invention may be crystallised or recrystallised from solvents such as organic solvents. In such cases solvates may be formed. This invention includes within its scope stoichiometric solvates including hydrates as well as compounds containing variable amounts of water that may be produced by processes such as lyophilisation.

Since the antibiotic compounds of the invention are intended for use in pharmaceutical compositions it will readily be understood that they are each provided in substantially pure form, for example at least 60% pure, more suitably at least 75% pure and preferably at least 85%, especially at least 95% pure, particularly at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 49% of a compound of the formula (I) or salt thereof.

Preferred compounds of the present invention include:
[4-(2,6-Dichloro-benzyloxy)-phenylamino]-2-phenyl-acetic acid;
[4-(2-Chloro-5-hydroxy-benzylamino)phenoxy]-2-phenyl-acetic acid;
[4-(2,6-Dichloro-benzylamino)-phenoxy]-2-phenyl-acetic acid;
[4-(2,5-Dichloro-benzylamino)-phenoxy]-2-phenyl-acetic acid;
{4-[3-(1,1-Difluoro-methoxy)-benzylamino]-phenoxy}-2-phenyl-acetic acid and (4-{Bis-[3-(1,1-difluoro-methoxy)-benzyl]-amino}-phenoxy)-2-phenyl-acetic acid;
{[4(6-Chloro-benzo[1,3]dioxol-5-ylmethyl)-amino]-phenoxy}-2-phenyl-acetic acid and {4-[Bis-(6-chloro-benzo[1,3]dioxol-5-ylmethyl)-amino]-phenoxy}-2-phenyl-acetic acid;
{4-[Acetyl-(2,6-dichloro-benzyl)-amino]-phenoxy}-2-phenyl-acetic acid;
4-{2-(4-[Acetyl-(2,6-dichloro-benzyl)-amino]-phenoxy}-2-phenyl-ethanoylsulfamoyl)-benzoic acid methyl ester; and
4-(2-{4-[Acetyl-(2,-dichloro-benzyl)-amino]-phenoxy}-2-phenyl-ethanoylsulfamoyl)-benzoic acid.

METHODS OF PREPARATION

The present invention provides compounds of formula (I),

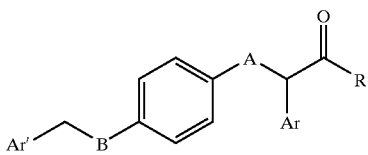
(I)

wherein R=OH, NHSO$_2$R"; A=NH, O; B=O, NR$^1$;
which can be prepared by reacting 4-nitrophenol with an aryl halide of Formula (2)

Ar'CH$_2$X (2)

in presence of a base such as cesium carbonate in an appropriate solvent such as N,N'-dimethylformate to afford a phenoxyether of Formula (3).

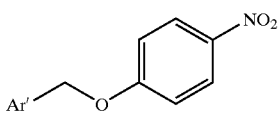
(3)

Reduction of the nitro function in a compound of Formula (3) with an appropriate reducing agent such as tin (II) chloride in a solvent such as ethanol at a certain temperature gives an aniline of Formula (4).

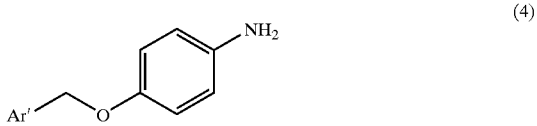
(4)

Reacting an aniline of Formula (4) with an alkyl α-haloarylacetic acetate of Formula (5)

(5)

provides an α-aminoacetic acetate derivative of Formula (6).

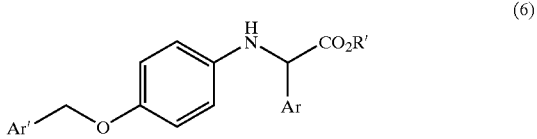
(6)

Hydrolysis of an ester of Formula (6) using a base such as lithium hydroxide in solvents such as tetrahydrofuran and water affords an acid of Formula (I), where R=OH,A=NH, B=O.

Reacting 4-amino-phenol with an alkyl α-haloarylacetic acetate of Formula (5) provides an α-phenoxyacetic acetate derivative of Formula (7).

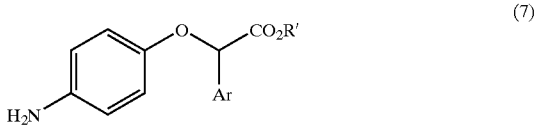
(7)

Alternatively, a compound of Formula (7) can be prepared by reacting 4-nitrophenol with a compound of Formula (5) followed by reducing the nitro group to the amino group under similar conditions described above.

Alkylation of an aniline derivative of Formula (7) with an aryl halide of Formula (2) in presence of a base such as cesium carbonate in an appropriate solvent such as N,N'-dimethylformate to afford a mono- and/or a di-alkylated compound(s) of Formula (8) and/or (9).

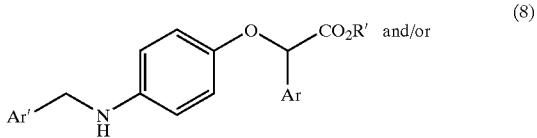
(8)

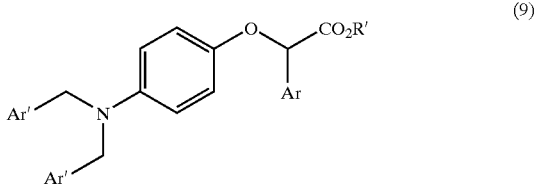
(9)

Hydrolysis of ester(s) of Formula (8) and/or (9) using a base such as lithium hydroxide in solvents such as tetrahydrofuran and water at certain temperature affords an acid of Formula (I), where R=OH, A=O, B=NR$^1$, R$^1$=H and/or Ar'CH$_2$.

Treatment of an aniline of Formula (I), where R=OH, A=O, B=NR$^1$, R$^1$=H, with acetic anhydride in presence of a base such as pyridine in a solvent such as dichloromethane gives an acylated compound of Formula (10).

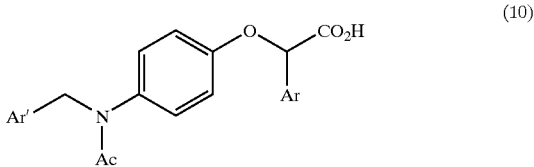
(10)

Coupling of an acid of Formula (10) with a sulfonamide of Formula (11)

R$^2$SO$_2$NH$_2$ (11)

using coupling reagents such as EDC and dimethylaminopyridine in an appropriate solvent such as dichloromethane affords an acyl sulfonamide of Formula (I), where R=HNSO$_2$R$^2$, A=O, B=NR$^1$, R$^1$=Ac. Any ester function in R' can be converted to an acid function using standard hydrolysis conditions described above.

SYNTHETIC EXAMPLES

The invention will now be described by reference to the following examples which are merely illustrative and are not to be construed as a limitation of the scope of the present invention. All temperatures are given in degrees centigrade, and all solvents arc highest available purity unless otherwise indicated.

Example 1

[4(2,6-Dichloro-benzyloxy)-phenylamino]2-phenyl-acetic acid

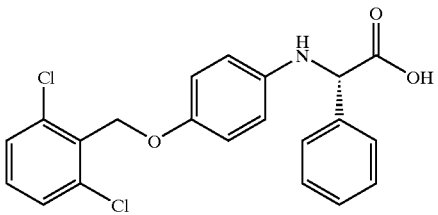

1(a) 4-nitro-(2,6Dichloro-benzyloxy)-phenylether

To a suspension of cesium carbonate (3.50 g, 10.80 mmol) in DMF (14 mL) was added 4nitrophenol (1.00 g, 7.19 mmol). After stirring at room temperature under argon for 30 minutes, 2,6-dichlorobenzyl bromide (1.30 g, 6.65 mmol) was added to the suspension and the resulting mixture was stirred at room temperature for 18 hours. The reaction was then quenched with water and extracted using a 1:1 mixture of hexane/EtOAc. The organic extracts were washed with water, sat'd ammonium chloride, brine, and dried over Na$_2$SO$_4$. After removing the solvent under reduced pressure, purification by flash column chromatography using an eluting system of hexane/EtOAc (90/10) yielded 1.90 g (96%) of the title compound as a white powder. $^1$H NMR (400 MHz, CDCl$_3$) δ8.24 (d, 2H), 7.41–7.06 (m, 5H), 5.37 (s, 2H). MH$^+$ 299.

1(b) 4-amino-(2,6-Dichloro-benzyloxy)-phenylether

To a solution of the compound from 1(a) (3.67 g, 12.30 mmol) in ethanol (120 mL) was added SnCl$_2$ (11.70 g, 61.60 mmol). The resulting suspension was stirred overnight under argon at 70° C. The solvent was then removed under reduced pressure to yield an off-white solid. The solid was then dissolved in EtOAc and NaHCO$_3$ was slowly added until a solid precipitated (approximately pH 8). The slurry was filtered through Celite, the filtrate was washed with brine, and dried over Na$_2$SO$_4$. After removing the solvent under reduced pressure, purification by flash column chromatography using an eluting system of hexane/EtOAc/Et$_3$N (75/24/1) yielded 2.37 g (72%) of the title compound as a burgundy oil. $^1$H NMR (400 MHz, CDCl$_3$) δ7.40–7.21 (m, 3H), 6.93 (d, 2H), 6.69 (d, 2H), 5.21 (s, 2H), 3.48 (s, 2H). MH$^+$ 269.

1(c) [4(2,6-Dichloro-benzyloxy)-phenylamino]-2-phenyl-acetic acid ethyl ester

A solution of the compound from 1(b) (143 mg, 0.58 mmol) and ethyl-alpha-bromophenylacetate (101 μL, 0.58 mmol) in DMF (6 mL) was stirred at 60° C. for 6.5 hours. The reaction was then quenched with water and extracted using a 3:1 mixture of EtOAc/hexane. The organic extracts were washed with water, brine, and dried over Na$_2$SO$_4$. After removing the solvent under reduced pressure, the crude product was used in the next reaction without further purification. MH$^+$ 431.

1(d) [4(2,6-Dichloro-benzyloxy)-phenylamino]-2-phenyl-acetic acid

To a solution of the compound from 1(c) (247 mg, 0.58 mmol) in THF (4.5 mL) and water (1.5 mL) was added lithium hydroxide monohydrate (120 mg, 2.88 mmol). The resulting solution was stirred at room temperature overnight. The solution was acidified with 1N HCl and the mixture was extracted with EtOAc. The organic extracts were washed with water, brine, and dried over Na$_2$SO$_4$. After removing the solvent under reduced pressure, purification by preparative HPLC yielded 25 mg (11%) of the title compound as white crystals. $^1$H NMR (400 MHz, d$_6$-DMSO) δ7.57–7.28 (m, 8H), 6.80 (d, 2H), 6.65 (d, 2H), 5.09 (s, 2H), 5.05 (s, 1H). MH$^+$ 403.

Example 2

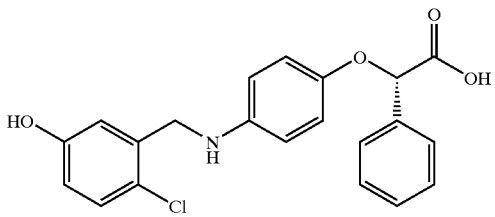

[4-(2-Chloro-5-hydroxy-benzylamino)-phenoxy]-2-phenyl-acetic acid

2(a) (4-Nitro-phenoxy)-2-phenyl-acetic acid ethyl ester

To a suspension of cesium carbonate (2.51 g, 7.70 mmol) in DMF (30 mL) was added 4-nitrophenol(1.07 g, 7.70 mmol). After stirring at room temperature under argon for 30 minutes, ethyl-alpha-bromophenylacetate (1.70 g, 7.00 mmol) was added to the suspension and the resulting mixture was stirred at room temperature overnight. The reaction was then quenched with water and extracted with EtOAc. The organic extracts were washed with water, brine, and dried over Na$_2$SO$_4$. After removing the solvent under reduced pressure, the crude product was used in the next reaction without further purification. ¹H NMR (400 MHz, CDC₃) δ8.20 (d, 2H) 7.60–7.37 (m, 5H), 7.05 (d, 2H), 5.70 (s, 1H), 4.20 (m, 2H), 1.22 (t, 3H). MH⁺ 303.

2(b) (4-Amino-phenoxy)-2-phenyl-acetic acid ethyl ester

Following the procedures of Example 1(b) except that the compound from 2(a) (750 mg, 2.48 mmol) was used in place of the compound from 1(a). Purification by flash column chromatography using an eluting system of hexane/EtOAc (60/40) yielded 0.45 g (67%) of the title compound. 1H NMR (400 MHz, CDCl₃) δ7.57–7.40 (m, 5H), 6.81 (d, 2H), 6.60 (d, 2H), 5.51 (s, 1H), 4.19 (m, 2H), 3.47 (s, 2H), 1.22 (t, 3H). MH⁺ 273.

2(c) [4(2-Chloro-5-hydroxy-benzylamino)-phenoxy]-2-phenyl-acetic acid ethyl ester To a solution of the compound from 2(b) (87 mg, 0.32 mmol) in DMF (2 mL) was added cesium carbonate (115 mg, 0.32 mmol). After stirring at room temperature under argon for one hour, (3-Bromomethyl-4chlorophenoxy)-tert-butyl-dimethyl-silane* (107 mg, 0.32 mmol) in DMF (1 mL) was then added and the suspension was stirred overnight. The reaction was quenched with sat'd ammonium chloride, extracted with 1:1 mixture of EtOAc/hexane. The organic extracts were washed with water, brine, and dried over Na₂SO₄. After removing the solvent under reduced pressure, the crude product was used in the next reaction without further purification. MH⁺ 413.

2(d) [4-(2-Chloro-5-hydroxy-benzylamino)-phenoxy]-2-phenyl-acetic acid

Following the procedures of Example 1(d) except that the compound from 2(c) (129 mg, 0.31 mmol) was used in place of the compound from 1(c). Purification by preparative HPLC yielded 14 mg (12%) of the title compound as a yellow gum. ¹H NMR (400 MHz, MeOD) δ7.59–6.80 (m, 12H), 5.76 (s, 1H), 4.49 (s, 2H) MH⁺ 385.

Example 3

[4-(2,6-Dichloro-benzylamino)-phenoxy]-2-phenyl-acetic acid

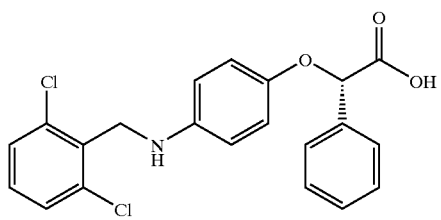

3(a) [4-(2,6-Dichloro-benzylamino)-phenoxy]-2phenyl-acetic acid ethyl ester

To a solution of the compound from 2(b) (125 mg, 0.46 mmol) and 1,3-Dichloro-2-chloromethyl-benzene (90.1 mg, 0.46 mmol) in DMF (5 mL) was added NaH (18.5 mg, 0.46 mmol) and stirred for 22 hours under argon at room temperature. The reaction was then quenched with water and extracted with EtOAc. The organic extracts were washed with water, sat'd ammonium chloride, brine, and dried over Na₂SO₄. After removing the solvent under reduced pressure, the crude product was used in the next reaction without further purification. MH⁺ 431

3(b).[4-(2,6-Dichloro-benzylamino)-phenoxy]-2-phenyl-acetic acid

Following the procedures of Example 1(d) except that the compound from 3(a) (150 mg, 0.35 mmol) was used in place of the compound from 1(c). Purification by preparative HPLC yielded 3 mg (2%) of the title compound as white crystals. ¹H NMR (400 MHz, MeOD) δ7.59–7.38 (m, 8H), 7.14 (d, 2H), 7.03 (d, 2H), 5.75 (s, 1H), 4.71 (s, 2H), 3.38 (s, 1H). MH⁺ 403

Example 4

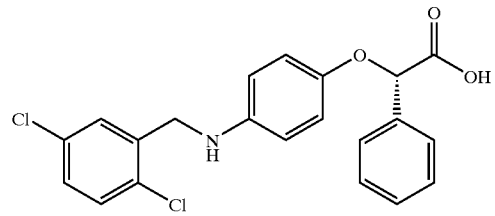

[4(2,5-Dichloro-benzylamino)-phenoxy]-2-phenyl-acetic acid

4(a) [4-(2,5-Dichloro-benzylamino)-phenoxy]-2-phenyl-acetic acid ethyl ester

A suspension of the compound from Example 2(b) (168 mg, 0.62 mmol), 2-Bromomethyl-1,4-dichloro-benzene (163 mg, 0.68 mmol), and cesium carbonate (222 mg, 0.68 mmol) in DMF (4 mL) was stirred under argon at room temperature overnight. The reaction was quenched with water, extracted with 1:1 mixture of EtOAc/hexane. The organic extracts were washed with water, brine, and dried over Na₂SO₄. After removing the solvent under reduced pressure, the crude product was used in the next reaction without further purification.

4(b) [4(2,5-Dichloro-benzylamino)-phenoxy]-2-phenyl-acetic acid

Following the procedures of Example 1(d) except that the compound from 4(a) (232 mg, 0.54 mmol) was used in place of the compound from 1(c). Purification by preparative HPLC yielded 20 mg (9%) of the title compound as white crystals. ¹H NMR (400 MHz, d₆-DMSO) δ7.55–7.32 (m, 8H), 6.79 (d, 2H), 6.49 (d, 2H), 6.05 (s, 1H), 5.59 (s, 1H), 4.29 (s, 2H). MH⁺ 403.

Example 5

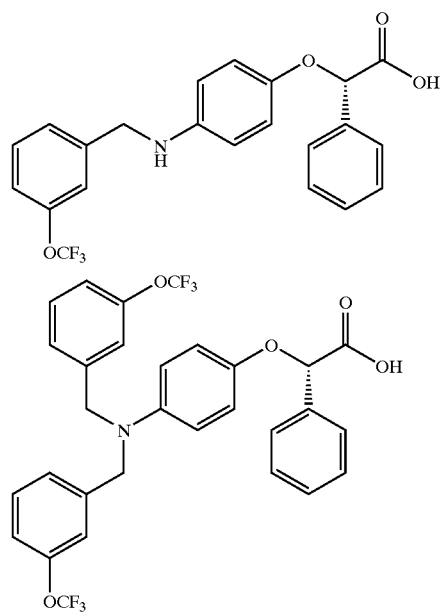

{4-[3-(1,1-Difluoro-methoxy)-benzylamino]-phenoxy}-2-phenyl-acetic acid and (4-{Bis-[3-(1,1difluoro-methoxy)-benzyl]-amino}-phenoxy)-2-phenyl-acetic acid 5(a) {4-[3-(1,1-Difluoro-methoxy)-benzylamino]-phenoxy}-2-phenyl-acetic acid ethyl ester and (4-{Bis-[3-(1,1-difluoro-methoxy)-benzyl]-amino)-phenoxy)-2-phenyl-acetic acid ethyl ester A suspension of the compound from Example 2(b) (100 mg, 0.37 mmol), 1-Bromomethyl-3-(1,1-difluoro-methoxy)-benzene (142 mg, 0.60 mmol), and cesium carbonate (222 mg, 0.68 mmol) in DMF (4 mL) was stirred under argon at room temperature overnight. The reaction was quenched with water, extracted with 1:1 mixture of ETOAc/hexane. The organic extracts were washed with water, brine, and dried over $Na_2SO_4$. After removing the solvent under reduced pressure, the crude product was used in the next reaction without further purification.

5(b) (4-[3-(1,1-Difluoro-methoxy)-benzylamino]-phenoxy}-2-phenyl-acetic acid) and (4-{Bis-[3-(1,1-difluoro-methoxy)-benzyl]-amino}-phenoxy)-2-phenyl-acetic acid Following the procedures of Example 1(d) except that the compound from 5(a) (221 mg, 0.52 mmol) was used in place of the compound from 1(c). Purification by preparative HPLC yielded 6 mg (3%) of the first title compound as white crystals. $^1$H NMR (400 MHz, d6-DMSO) δ7.55–7.13 (m, 9H), 7.03 (m, 1H), 6.75 (d, 2H), 6.50 (d, 2H), 5.58 (s, 1H), 4.20 (s, 2H). $MH^+$ 401. Purification by preparative HPLC yielded 20 mg (7%) of the second title compound as brown gum. $^1$H NMR (400 MHz, $CDCl_3$) δ7.55–6.78 (m, 17H), 6.38 (t, 2H), 5.52 (s, 1H), 4.65 (s, 4H). $MH^+$ 557.

Example 6

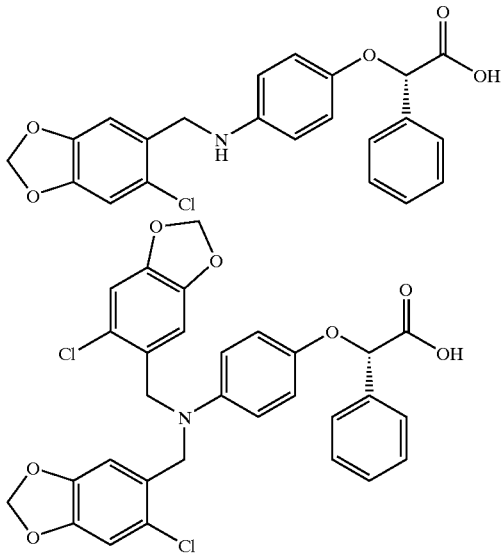

{4-[(6-Chloro-benzo[1,3]dioxol-5-ylmethyl)-amino]-phenoxy}-2-phenyl-acetic acid and {4-[Bis-(6-chloro-benzo[1,3]dioxol-5-ylmethyl)-amino]-phenoxy}-2-phenyl-acetic acid.

6(a) {4-[(6-Chloro-benzo[1,3]dioxol-5-ylmethyl)-amino]-phenoxy}-2-phenyl-acetic acid ethyl ester and {4-[Bis-(6-chloro-benzo[1,3]dioxol-5-ylmethyl)-amino]-phenoxy}-2-phenyl-acetic acid ethyl ester.

A suspension of the compound from Example 2(b) (100 mg, 0.37 mmol), 5-Chloro-6-chloromethyl]-benzo[1,3] dioxole (128 mg, 0.62 mmol), and cesium carbonate (222 mg, 0.68 mmol) in DMF (4 mL) was stirred under argon at room temperature overnight. The reaction was quenched with water, extracted with 1:1 mixture of EtOAc/hexane. The organic extracts were washed with water, brine, and dried over $Na_2SO_4$. After removing the solvent under reduced pressure, the crude product was used in the next reaction without further purification.

6(b) {4-[(6-Chloro-benzo[1,3]dioxol-5-ylmethyl)-amino]-phenoxy}-2-phenyl-acetic acid and {4-[Bis-(6chloro-benzo[1,3]dioxol-5-ylmethyl)amino]phenoxy}-2-phenyl-acetic acid Following the procedures of Example 1(d) except that the compound from 6(a) (207 mg, 0.47 mmol) was used in place of the compound from 1(c). Purification by preparative HPLC yielded 10 mg (5%) of the first title compound as white crystals. $^1$H NMR (400 MHz, $d_6$-DMSO) δ7.53 (δ, 2H), 7.40 (m, 3H), 7.09 (s, 1H), 6.92 (s, 1H), 6.76 (d, 2H), 6.48 (d, 2H), 6.04 (s, 2H), 5.60 (s, 1H), 4.18 (s, 2H).$MH^+$ 413. Purification by preparative HPLC yielded 20 mg (7%) of the second title compound as a brown gum. $^1$H NMR (400 MHz, $CDCl_3$) δ7.59–7.35 (m, 5H), 6.89–6.61 (m, 8H), 5.95 (s, 4H), 5.50 (s, 1H), 4.55 (s, 4H).$MH^+$ 581.

Example 7

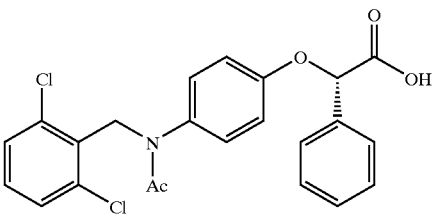

{4-[Acetyl-(2,6-dichloro-benzyl)-amino]-phenoxy}-2-phenyl-acetic acid

7(a) {4-[Acetyl-(2,6-dichloro-benzyl)-amino]-phenoxy}-2-phenyl-acetic acid

To a solution of the compound from Example 3(b) (200 mg, 0.49 mmol) in methylene chloride (5 mL) was added pyridine (0.12 mL) and acetic anhydride (0.094 mL) and stirred at room temperature overnight. The reaction was quenched with water and extracted with EtOAc. The organic extracts were washed with water, brine, and dried over $Na_2SO_4$. Purification by preparative HPLC yielded 30 mg (7%) of the title compound as a yellow gum. $^1$H NMR (400 MHz, $CDCl_3$) δ7.58 (d, 2H), 7.436–675 (m, 10H), 5.58 (s, 1H), 5.23 (s, 2H), 1.81 (s, 3H). $MH^+$ 445.

Example 8

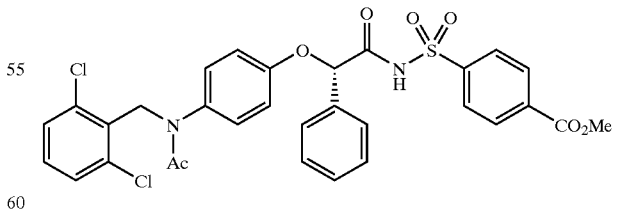

4-(2-{4-[Acetyl-(2,6dichloro-benzyl)-amino]-phenoxy}-2-phenyl-ethanoylsulfamoyl)-benzoic acid methyl ester 8(a) 4-Sulfamoyl-benzoic acid methyl ester To a solution of KOH (108 mg, 2.0 mmol) in water (1 mL) was added $Et_2O$ and cooled to 0° C. MNNG (292 mg, 1.99 mmol) was added and the resulting yellow solution was added to a suspension of 4-Sulfamoyl-benzoic acid in Et$_2$O at room temperature and stirred overnight. The reaction was quenched with acetic acid and the resulting mixture was diluted with water. The mixture was then extracted with ethyl acetate and the combined organic extracts was washed with bine and dried over Na$_2$SO$_4$. Removal of solvent gave the crude product which was used in the next reaction without further purification. $^1$H NMR (400 MHz, MeOD) δ8.17 (d, 2H), 8.00 (d, 2H), 3.92 (s, 3H).

8(b) 4-(2-{4-[Acetyl-(2,6-dichloro-benzyl)-amino]-phenoxy}-2-phenyl-ethanoylsulfamoyl)-benzoic acid methyl ester To a solution of the compound from Example 7(a) (102 mg, 0.23 mmol), DMAP (28 mg, 0.23 mmol) and the compound from 8(a)(49 mg, 0.23 mmol) in methylene chloride (3.5 mL) was added EDC (44 mg, 0.23 mmol) and stirred at room temperature for 35 hours. The reaction was quenched with 1N HCl, extracted with CH$_2$Cl$_2$, washed with brine and dried over Na$_2$SO$_4$. Purification by preparative HPLC yielded 12 mg (8%) of the title compound as a white powder. $^1$H NMR (400 MHz, CDCl$_3$) δ9.27 (s, 1H), 8.14 (d, 2H), 8.05 (d, 2H), 7.35–7.02 (m, 8H), 6.91 (d, 2H), 6.57 (d, 2H), 5.43 (s, 1H), 5.21 (s, 2H), 3.95 (s,3H), 1.80 (s, 3H). MH$^+$ 642.

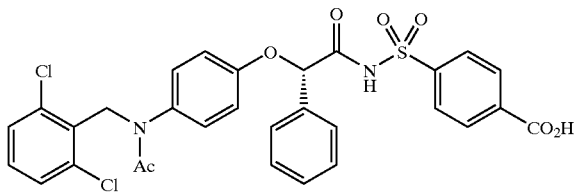

Example 9

4-(2-{4-[Acetyl-(2,6-dichloro-benzyl)-amino]-phenoxy}-2-phenyl-ethanoylsulfamoyl)-benzoic acid 9(a) 4-Sulfamoyl-benzoic acid allyl ester To a suspension of 4-Sulfamoyl-benzoic acid (2.0 g, 9.94 mmol) and sodium bicarbonate (0.84 g, 9.94 mmol) in DMF (20 mL) was added allyl iodide (0.91 mL, 9.94 mmol) and stirred at room temperature overnight under argon. The reaction was quenched with water, extracted with EtOAc and dried over Na$_2$SO$_4$. After removing the solvent under reduced pressure, the crude product was used in the next reaction without further purification. $^1$H NMR (400 MHz, CDCl$_3$) δ8.20 (d, 2H), 8.00 (d, 2H), 6.06 (m, 1H), 5.40 dd, 2H), 5.02 (s, 2H), 4.96 (d, 2H). MH$^+$ 243.

9(b) 4-(2-{4-[Acetyl-(2,6dichloro-benzyl)-amino]-phenoxy}-2-phenyl-ethanoylsulfamoyl)-benzoic acid allyl ester Following the procedures of Example 8(b) except that the compound from 9(a) (241 mg, 1.0 mmol) was used in place of 4-Sulfamoyl-benzoic acid methyl ester. The crude product was used in the next reaction without further purification. MH$^+$ 668.

9(c) 4-(2-{4-[Acetyl-(2,6-dichloro-benzyl)-amino]-phenoxy}2-phenyl-ethanoylsulfamoyl)-benzoic acid Following the procedures of Example 1(d) except that the compound from 9(b) (100 mg, 0.15 mmol) was used in place of the compound from 1(c). Purification by preparative HPLC yielded 10 mg (11%) of the title compound as a white powder. $^1$ H NMR (400 MHz, MeOD) δ8.11 (d, 2H), 7.96 (d, 2H), 7.41–7.12 (m, 8H), 6.90 (d, 2H), 6.75 (d, 2H), 5.53 (s, 1H), 5.21 (q, 2H), 1.79 (s, 3H). MH$^+$ 628.

Biological Assay

FabH was assayed in a coupled format using his-tagged *S. aureus* FabD, and acyl carrier protein (ACP) purchased from Sigma. Lyophilized ACP was reduced using β-mercaptoethanol in phosphate buffer. Malonyl-CoA, and FabD were added to the reduced ACP, thus generating malonyl-ACP. After the FabD reaction reached equilibrium, [$^{14}$C] acetyl-CoA and inhibitors were added, and the reaction started by the addition of FabH. TCA precipitation and filtration was used to separate [$^{14}$C] acetyl-CoA substrate from [$^{14}$C] acetoacetyl-ACP product.

Secondary and tertiary screens of suitable reproducibility, sensitivity, throughput and analytical power to progress primary screen hits are characterized, validated and in current use. Compounds are evaluated against purified mammalian fatty acid biosynthetic enzymes, *E. coli* FabH, FabB and a human lung cell cytotoxicity assay.

In addition, whole-cell antibacterial activity is determined against a range of clinically relevant wild type and efflux impaired bacteria using standard and novel fluorescence based technologies. The FabH assay has been thoroughly characterized kinetically and a reaction mechanism proposed. Detailed studies have generated novel data about mechanism of inhibition by tool compounds, including thiolactomycin. Screens in use are of direct relevance to the therapeutic goal-eradication of bacteria from sites of infection ('cure'). Several state-of-the-art animal models of bacterial infection are available, meaningful and in current use in this and numerous other studies at SB. Extensive prior experience with known antibacterials confirm that bacterial kill in vitro and in animal models is an excellent indicator of bacterial kill in vivo and cure of infection.

The present invention also provides a pharmaceutical composition, which comprises a compound of formula (I) or a pharmaceutically acceptable salt or in vivo hydrolysable ester thereof, and a pharmaceutically acceptable carrier. The compositions of the invention include those in a form adapted for oral, topical or parenteral use and may be used for the treatment of bacterial infection in mammals including humans.

The antibiotic compounds according to the invention may be formulated for administration in any convenient way for use in human or veterinary medicine, by analogy with other antibiotics.

The composition may be formulated for administration by any route, such as oral, topical or parenteral, especially oral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica;

disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. The solution preferably contains a buffer (such as phosphate) to keep the pH in the range of about 3.5 to 7. DMSO or alcoholic solvents may also be present (at concentrations such as 0.01 to 10 mL/liter) to aid solubility and penetration of the compound of Formula (I) Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 1 to 140 mg/kg of body weight, depending on the route and frequency of administration. Inhibitors of β-ketoacyl-ACP Synthase (FabH) can be administered by injection in solutions either intravenously, intramuscularly, intraperitoneally, or orally. The solution preferably contains a buffer (such as phosphate) to keep the pH in the range of about 3.5 to 7. DMSO or alcoholic solvents may also be present (at concentrations such as 0.01 to 10 mL/liter) to aid solubility and penetration of the β-ketoacyl-ACP Synthase (FabH) inhibitor.

No unacceptable toxicological effects are expected when a compound of formula (Ia) or a pharmaceutically acceptable salt or in vivo hydrolysable ester thereof is administered in the above-mentioned dosage range.

The compound of formula (I) may be the sole therapeutic agent in the compositions of the invention or a combination with other antibiotics or compounds which enhance the antibacterial activity of a compound of formula (I) may be employed.

The antibiotic compounds of the present invention are active against a wide range of organisms including both Gram-negative organisms such as *Escherichia coli* and *Klebsiella pneumoniae* and Gram-positive organisms such as *Staphylococcus aureus, Streptococcus pneumoniae, Enterococcus faecalis* and *Enterococcus faecium*, including isolates resistant to existing antibiotics.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the area can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound according to Formula (I):

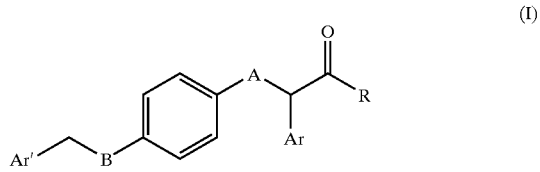

wherein:

R represents OH, or NHSO$_2$R$^2$;

A represents NH or O;

B represents O, or NR$^1$;

R$^1$ represents Ar'alkyl, or AlkylCO;

Ar and Ar'represent, independently, phenyl, thiophenyl, pyridinyl, or pyrimidinyl, all of which could be substituted with a substituting selected from the group consisting of: halo, including fluoro, bromo, chloro, iodo, NO$_2$, CN, CO$_2$R$^3$, OR$^3$, NR$^3$R$^4$, C$_{1-10}$alkyl, C$_{1-10}$alkoxy, aryloxy, arylalkoxy, and heteroaryloxy;

R$^2$ represents alkyl, Ar'alkyl, or Ar'; and

R$^3$ and R$^4$ represent, independently, hydrogen, or C$_{1-10}$alkyl;

or a pharmaceutically acceptable salt thereof or a pharmaceutically acceptable salt complex thereof.

2. A compound according to claim 1 selected from the group consisting of:

[4-(2,6-Dichloro-benzyloxy)-phenylamino]-2-phenyl-acetic acid;

[4-(2-Chloro-5-hydroxy-benzylamino)-phenoxy]-2-phenyl-acetic acid;

[4-(2,6-Dichloro-benzylamino)-phenoxy]-2-phenyl-acetic acid;

[4-(2,5-Dichloro-benzylamino)-phenoxy]-2-phenyl-acetic acid;

{4-[3-(1,1-Difluoro-methoxy)-benzylamino]-phenoxy}-2-phenyl-acetic acid and (4-{Bis-[3-(1,1-difluoro-methoxy)benzyl]-amino}-phenoxy)-2-phenyl-acetic acid;

{4-[(6-Chloro-benzo[1,3]dioxol-5-ylmethyl)-amino]-phenoxy}-2-phenyl-acetic acid and {4-[Bis-(6-chloro-benzo[1,3]dioxol-5-ylmethyl)-amino]-phenoxy}-2-phenyl-acetic acid;

{4-[Acetyl-(2,6-dichloro-benzyl)-amino]-phenoxy}-2-phenyl-acetic acid;

4-(2-{4-[Acetyl-(2,6-dichloro-benzyl)-amino]-phenoxy}-2-phenyl-ethanoylsulfamoyl)-benzoic acid methyl ester; and 4-(2-{4-[Acetyl-(2,6-dichloro-benzyl)-amino]-phenoxy}-2-phenyl-ethanoylsulfamoyl)-benzoic acid.

3. A method of treating bacterial infections by administering to a patient in need thereof an effective amount of a compound of Formula (I) according to claim 1.

4. A method of treatment according to claim 1 wherein the compound of Formula (I) is selected from the group consisting of:

[4(2,6-Dichloro-benzyloxy)-phenylamino]-2-phenyl-acetic acid;

[4-(2-Chloro-5-hydroxy-benzylamino)-phenoxy]-2-phenyl-acetic acid;

[4-(2,6-Dichloro-benzylamino)-phenoxy]-2-phenyl-acetic acid;

[4-(2,5-Dichloro-benzylamino)-phenoxy]-2-phenyl-acetic acid;

{4-[3-(1,1-Difluoro-methoxy)-benzylamino]-phenoxy}-2-phenyl-acetic acid and (4-{Bis-[3-(11-difluoromethoxy)-benzyl]-amino}-phenoxy)-2-phenyl-acetic acid;

{4-[(6-Chloro-benzo[1,3]dioxol-5-ylmethyl)-amino]-phenoxy}-2-phenyl-acetic acid and {4-[Bis-(6-chloro-benzo[1,3]dioxol-5-ylmethyl)-amino]-phenoxy}-2-phenyl-acetic acid;

{4-[Acetyl-(2,6-dichloro-benzyl)-amino]-phenoxy}-2-phenyl-acetic acid;

4-(2-{4-[Acetyl-(2,6-dichloro-benzyl)-amino]-phenoxy}-2-phenyl-ethanoylsulfamoyl)-benzoic acid methyl ester; and 4-(2-{4-[Acetyl-(2,6-dichloro-benzyl)-amino]-phenoxy}-2-phenyl-ethanoylsulfamoyl)-benzoic acid.

* * * * *